United States Patent [19]

Brian et al.

[11] Patent Number: 5,202,430
[45] Date of Patent: Apr. 13, 1993

[54] TRANSMISSIBLE GASTROENTERITIS VIRUS GENES

[75] Inventors: David A. Brian, Knoxville, Tenn.; Paul A. Kapke, Ames, Iowa

[73] Assignee: University of Tennessee, Knoxville, Tenn.

[21] Appl. No.: 639,404

[22] Filed: Jan. 10, 1991

Related U.S. Application Data

[63] Continuation of Ser. No. 465,570, Jan. 16, 1990, abandoned, which is a continuation of Ser. No. 41,704, Apr. 23, 1987, abandoned.

[51] Int. Cl.$^5$ ............................................. C07H 17/00
[52] U.S. Cl. .................................... 536/23.72; 435/6; 435/69.3; 435/91; 435/235.1; 436/811; 935/9; 935/32; 935/78
[58] Field of Search ............... 435/6, 91, 235.1, 69.3; 436/811; 536/27; 935/32, 78, 9

[56] References Cited

FOREIGN PATENT DOCUMENTS 0138242 4/1985 European Pat. Off. .

OTHER PUBLICATIONS

Wesley et al. (1986) J. Gen. Virology, vol. 67, pp. 1419-1425.
Dennis et al. (1982) J. of Virology, vol. 42, No. 1, pp. 153-164.
Garwes et al. (1979) Veterinary Microbiology, vol. 3, pp. 179-190.
Budzilowicz et al. (1985) J. of Virology, vol. 53, No. 3, pp. 834-840.
Brian et al. (1980) J. of Virology, vol. 34, No. 2, pp. 410-415.
Garwes et al. (1975) J. of Gen. Virology, vol. 29, pp. 25-34.
Brian et al. (1983) Proceedings of the Fourth Int'l Symposium on Neonatal Diarrhea, Univ. of Saskatchewan, pp. 100-115.
Kapke et al. (1986) Virology, vol. 151, pp. 41-49.
Laude et al. (1987) J. Gen. Virol., vol. 68, pp. 1687-1693.
Hu et al. (1984) in *Modern Approaches to Vaccines* (Ed: Chanock et al., Cold Spring Harbor Laboratory, Cold Spring Harbor, N.Y.), pp. 219-233.

Primary Examiner—Margaret Moskowitz
Assistant Examiner—Ardin H. Marschel
Attorney, Agent, or Firm—Paul J. Koivuniemi; Gregory W. Steele

[57] ABSTRACT

The present invention provides recombinant DNA molecules comprising a sequence encoding a transmissible gastroenteritis virus polypeptide selected from the group consisting of M, N and P, host cells transformed by said recombinant DNA molecule sequences, the M, N and P polypeptides. The present invention also provides subunit vaccines for TGEV.

4 Claims, No Drawings

TRANSMISSIBLE GASTROENTERITIS VIRUS GENES

FIELD OF INVENTION

This application is a continuation of Ser. No. 07/465,570, filed Jan. 16, 1990, now abandoned, which is a continuation of Ser. No. 07/041,707, filed Apr. 23, 1987, now abandoned.

This invention relates to recombinant DNA. More specifically, the invention relates to DNA sequences encoding transmissible gastroenteritis virus proteins and polypeptides related thereto. These DNA sequences are useful fro screening animals to determine whether they are infected with transmissible gastroenteritis virus and also for expressing the polypeptides encoded thereby.

BACKGROUND OF THE INVENTION

Transmissible gastroenteritis virus (TGEV) is a highly contagious, enteric disease of swine characterized by vomiting, severe diarrhea, and a high mortality in piglets under two weeks old. Although swine of all ages are susceptible to TGEV, the mortality rate in swine over five weeks old is very low.

The first reported occurrence of TGEV in the United States was in 1945. Subsequent to its recognition in the United States, TGEV has been reported in Japan, England, many European countries, Taiwan. Central and South America and Canada.

In the densely swine-populated areas of the midwestern United States, TGEV is recognized as one of the major causes of sickness and death in piglets. "Swine producers are especially apprehensive about this disease because (1) mortality is high in newborn pigs; (2) there is no effective, practical treatment; (3) entrance of the virus into a herd in winter months is difficult to prevent because of the probable role of birds, especially starlings; and (4) the commercial vaccine available (1979) is of limited effectiveness." (E H. Bohl, "Transmissible Gastroenteritis", in *Diseases of Swine.* A.D. Leman et al, eds., 5th edition (1981)).

For a detailed review of TGEV see Bohl, supra.

Porcine TGEV is a coronavirus. One major problem with coronavirus infections is the unavailability of a rapid and efficient means for identifying and quantifying viruses in infected animals. Such a test is important not only for differentiating coronaviruses from other agents that cause similar disease, but also for determining the mechanism by which coronaviruses perpetuate enzootic or epizootic outbreaks. A sensitive test is also needed to determine the role of coronaviruses in acute enteric diseases of man, putative zoonoses, and chronic diseases of animals and man for which causes are not yet known. Further, an effective TGEV vaccine comprising a TGEV polypeptide would also be useful. Some of the polypeptides of the instant invention function as such vaccines.

INFORMATION DISCLOSURE

The genome of TGEV is a single-stranded, non-segmented, polyadenylated, infectious RNA molecule of 6.8 x 106 MW or approximately 20 kb in length (D A Brian et al., J. Virol., 34, pp. 410–15 (1980)). The total number of genes encoded by the TGEV genome, however, has not yet been determined. The genome codes for at least four unique proteins. The virion is comprised of three major structural proteins: a 200-kd peplomeric glycoprotein (also known as P, spike protein or E2), a 29, kd membrane-associated matrix glyco-protein (M or El), and an internal phosphorylated nucleocapsid protein (N) that measures from 46 to 50 kd (D. J. Garwes and D H. Pocock, J. Gen Virol., 29, p. 25 (1975); (D.A. Brian et al., in "Proceedings from the Fourth International Symposium on Neonatal Diarrhea", D.D. Acres. ed. (1983); P.A. Kapke and D.A. Brian, Virology, 151, pp. 41–49 (1986) which is incorporated herein by reference; R.D. Wesley and R.D. Woods, J. Gen. Virol., 67, pp 1419-25 (1986)). These proteins alone account for only about 8.4 kb of coding information. In addition, the virus synthesizes at least one nonstructural protein during its replication, an RNA-dependent RNA polymerase, the size of which is not yet known (D E. Dennis and D. A. Brian, J. Virol., 42, pp. 153–64 (1982)). During replication. TGEV produces nine species of subgenome-size polyadenylated RNA molecules.

While the 200 Kd P glycoprotein appears to be important in stimulating neutralizing antibody (D.J. Garwes et al., Vet. Micro-biol., 3, p. 179 (1978)), the 29 Kd M glycoprotein ma important, especially if complement is part of the virus-antibody reaction (R. Wood et al., Asilomar (September 1986)).

We have prepared cDNA clones beginning from the polyadenylated 3' end of the TGEV genome and examined the sequences of potential genes (Kapke and Brian, supra). Within the first (3') 2000 bases we deduced, from an examination of open reading frames, a noncoding region of 276 bases, and genes for a 9101 MW hypothetical hydrophobic polypeptide, a 43,426 MW nucleocapsid protein, and part of a matrix protein, arranged in that order from the 3' end of the genome (Kapke and Brian, supra) Assuming that a conserved intergenic sequence would be found in TGEV as has been found in the mouse hepatitis coronavirus (MHV) (C.J. Budzilowicz et al., J. Virol., 53, p. 834 (1985)) and the avian infectious bronchitis coronavirus (IBV), we prepared a synthetic oligonucleotide that is complementary to the TGEV intergenic sequence and used it as a primer for first-strand DNA synthesis for the preparation of additional genomic cDNA clones. Several cDNA clones were thus prepared and seven that mapped within the first (3') 2601 bases were sequenced in part and another clone was sequenced completely to derive a gene sequence for the M protein.

SUMMARY OF THE INVENTION

The present invention provides recombinant DNA molecules comprising DNA sequences encoding polypeptides displaying TGEV immunogenicity.

More particularly, the present invention provides host cells transformed with recombinant DNA molecules comprising the DNA sequences set forth in Charts A and B, and fragments thereof.

The present invention also provides polypeptides expressed by hosts transformed with recombinant DNA molecules comprising DNA sequences of the formulas set forth in Charts A and B, and immunologically functional equivalents and immunogenic fragments and derivatives of the polypeptides.

More particularly, the present invention provides polypeptides having the formulas set forth in Charts A and B immunogenic fragments thereof and immunologically functional equivalents thereof.

The present invention also provides recombinant DNA molecules comprising the DNA sequences encoding TGEV nucleocapsid and M proteins or immunogenic fragments thereof.

The present invention also provides a method for detecting TGEV infections in animals comprising contacting a DNA sequence of the present invention with fluid from an animal to be diagnosed.

DETAILED DESCRIPTION OF THE INVENTION

As used herein, immunogenicity and antigenicity are used inter-changeably to refer to the ability to stimulate any type of adaptive immune response, i.e., antigen and antigenicity are not limited in meaning to substances that stimulate the production of antibodies.

Most of the recombinant DNA methods employed in practicing the present invention are standard procedures, well known to those skilled in the art, and described in detail, for example, in Molecular Cloning, T. Maniatis, et al., Cold Spring Harbor Laboratory, (1982) and B. Perbal, A Practical Guide to Molecular Cloning. John Wiley & Sons (1984), which are incorporated herein by reference.

EXAMPLES

Example 1

The Nucleocapsid Protein of TGEV

In this example we describe the cloning and sequencing of a portion of the TGEV genome comprising the N gene. cDNA clones were prepared from the 3' terminal 10% of the polyadenylated genome and were sequenced. Two potential genes were identified within the first 1663 bases. One gene encodes a protein of 382 amino acids which is the nucleocapsid protein on the basis of size, chemical properties, and significant amino acid sequence homology with other coronavirus nucleocapsid proteins. This gene is flanked on its immediate 5' side by at least part of the matrix protein gene (Example 2). The second gene lies to the 3' side of the nucleocapsid protein gene and encodes a protein of 78 amino acids that is hydrophobic at both ends A 3' noncoding sequence of 276 bases sharing a 9-base conserved sequence near the poly A tail with other coronaviruses was also determined. Virus and Cells.

The Purdue strain of TGEV was plaque purified and grown on the swine testicle (ST) cell line as previously described (Brian et al., supra).

Purification of Genomic RNA

Virus was purified from clarified supernatant fluids as previously described (Brian et al , supra) except that all sucrose solutions were made up in TMEN (10 mM Tris-maleate, pH 6 0, 100 mM NaCl, 1 mM EDTA). Viral RNA in 1 of 10 flasks was radiolabeled in order to follow the purification of the RNA. For these radiolabeled cultures, infected cells were refed with phosphate-free medium containing 1% fetal calf serum and 40 μCi [$^{32}$P]orthophosphate (ICN) per milliliter. Viral RNA was extracted by dissolving the virus pellet in 0.5 ml TNE (10 mM Tris-hydrochloride, pH 7.5, 100 mM NaCl, 1 mM EDTA) containing 1% SDS and 0.5 mg proteinase K per milliliter, incubating for 0.5 hr at 37° and extracting twice with an equal volume of a mixture of 50% phenol/48% chloroform/2% isoamyl alcohol. RNA was ethanol precipitated after adding 0.1 volume 2M sodium acetate. Because small molecular weight RNA species are found in some preparations of purified coronavirion RNA, full-length genomic RNA to be used for cDNA cloning and making probes for colony screening was selected by rate-zonal sedimentation on preformed linear gradients of 15 to 30% sucrose (wt/wt) made up in TNE-0.1% SDS. RNA was dissolved in water and sedimented 1.5 hr at 110,000 g, 25°, on 5-ml gradients. Fractions of 0.2 ml were collected and the distribution of radioactivity was determined by Cerenkov counting Only RNA sedimenting with a sedimentation coefficient of 50 S or greater, as determined by reference to sedimentation of mammalian 28 S and 18 S ribosomal RNA in a parallel gradient, was recovered by ethanol precipitation and used in the experiments described below. cDNA Cloning of the 3 ' End of the TGEV Genome TGEV genomic RNA was cloned using a modified method of U. Gubler and B. J. Hoffman, Gene, 25, p. 263 (1983). First strand synthesis was carried out in a reaction volume of 50 μl containing 50 mM Tris-hydrochloride, pH 8.3, 10 mM $MgCl_2$, 10 mM DT 2 mM dATP, 2 mM dCTP, 10 μCi [$^{32}$P]dCTP (3000 Ci/mmol, ICN), 50 pmol oligo $dT_{12-18}$6 μg TGEV RNA, 30 U RNAsin, 10 U reverse transcriptase (Seikagaku), for 1 hr at 42°, and the reaction was stopped by adding 2 μl 0.5 M EDTA. Nucleic acids were phenol-chloroform-isoamyl alcohol extracted and ethanol precipitated after the addition of 0.5 vol of 7.5M ammonium acetate.

Second strand synthesis was carried out in a reaction volume of 100 μl containing 20 mM Tris-hydrochloride, pH 7.5, 5 mM $MgCl_2$, 10 mM $(NH_4)_2SO_4$, 100 mM KCl, 0.15 mM β-AND. 50 mg/ml BSA. 40 μM dNTPs. 8.5 U/ml *Escherichia coli* RNAse H. 230 U/ml DNA polymerase I, 10 U/ml DNA ligase, adn all of the product from the first strand reaction. The reaction was incubated at 12° for 1 hour, then at 22° for 1 hour. The reaction was stopped by adding 4 μl 0.5M EDTA and reaction products were phenol-chloroform-isoamyl alcohol extracted and fractionated on a Sephadex G50 spun column (Maniatis et al., supra), and the double-stranded (ds) cDNA was ethanol precipitated.

Double-stranded cDNA was homopolymer tailed essentially by the method of R. Roychoudhury and R. Wu, Meth. Enz., 65, pp. 43–62 (1980). The following were added together, in order: 3 μl $dCTP^{32}$ (>800 Ci/mmol), 20 μl 10 X cacodylate buffer (1.4 mM potassium cacodylate, 0.3M Tris-hydrochloride, pH 7.6), 4 μl 5 mM DTT, 3 μl 10 mM dCTP, 2 μl 100 mM $CoCl_2$, 12 units terminal deoxynucleotide transferase (PL Biochemicals; at least 8 units/pmol 3' end) in 1.5 μl, $H_2O$ to 200 μl final volume. The reaction was carried out at 12° for 1.5 min then stopped by adding 10 μl 0.5M EDTA This reaction resulted in an average of 15 dCMP residues added per 3' end of dsDNA, the optimal number for annealing and transformation (Peacock et al., Bioch. Biophys. Acta, 655, pp. 243–50 (1981)

C-tailed ds cDNA was annealed to G-tailed, PstI-linearized pUC9 vector (PL Biochemicals) for 4 hours at 58° in a 50 μl vol of buffer containing 10 mM Tris-hydrochloride, pH 7.5, 150 mM NaCl. 1 mM EDTA. The total concentration of DNA used was less than 0.5 μg/ml and the optimal insert:vector ratio was 1:1 on a mass basis. E. coli strain JM103 was transformed using the method of D. Hanahan, J. Mol. Biol., 166, pp. 557–80 (1983). Cells containing inserts were observed as white colonies on YT agar plates that contained 100 μg ampicillin/ml, 1 mM IPTG, and 0.004% X-gal (G. Heidecker and J. Messing. Nucl. Acids Res., 11, pp. 4891–4906 (1983)). Recombinant colonies were transferred to nitrocellulose (Millipore, HAWP) and probed with random-primed cDNA copied from TGEV genomic RNA.

Identification of Large Clones Containing 3'-Specific TGEV Sequences $^{32}$P-labeled, random-primed cDNA used for colony hybridization was synthesized as described above for the oligo(dT)-primed reaction except that 0.2 μg of RNA was used and oligo(dT) was replaced by 20 μg of fragmented calf thymus DNA. Probe was alkali treated to hydrolyze the RNA and then was used for colony hybridization (Maniatis et al, supra). Colonies yielding a strong signal were analyzed for insert size by electrophoresis of plasmid DNA in agarose gels (C.I. Kado and S.T. Liu. J. Bacteriol., 145, pp. 1365–73 (1981)). Inserts of 0.2 to 2.0 kb (the largest) were further analyzed by Southern hybridization with $^{32}$P-labeled poly(dT) to detect poly(dA) content and by cross-hybridization with nick-translated inserts to detect overlapping sequences. $^{32}$P-labeled poly(dT) probe was prepared as described above for the oligo(dT)-primed reaction except that 50 pmol oligo(dT).poly(rA) (PL Biochemicals) replaced the RNA. Alkali-treated $^{32}$P-labeled poly(dT) probe was incubated for hybridization at 37° for 12 hr then at 20° for 36 hr. and blots were washed in 2 × SSC, 0.1% SDS at 20°.

Restriction Endonuclease Mapping

Plasmids were purified by lysozyme lysis and cesium chloride centrifugation (Maniatis et al., supra). and restriction endonuclease mapping was done essentially as described by H.O. Smith and M.L. Bernstiel, Nucl. Acids Res., 3, pp. 2387–98 (1976) using plasmids that were labeled at the Sal I site within the multiple cloning linker region.

DNA Sequencing and Sequence Analysis

Restriction fragments end-labeled with $^{32}$P were isolated and sequenced by the method of A M. Maxam and W. Gilbert, Meth. Enz., 65 pp. 499–560 (1980). Sequences were analyzed with the aid of the program developed by C. Queen and L.J. Korn. Nucl. Acids Res., 12, pp. 581–99 (1984) and sequence homologies were searched against Genbank (Beckman Microgenie program, March 1985 version, Beckman Instruments, Inc.).

cDNA Cloning and Sequencing of Two Clones from the 3' End of the Genome

Starting material for cDNA cloning was approximately 6 μg of rate-zonally purified genomic RNA obtained from 400 ml of tissue culture medium. An estimated 200 ng of ds cDNA was obtained as determined by radiolabel incorporation during second strand synthesis, and from this approximately 2000 white colonies were obtained. By colony screening, 200 colonies gave a strong signal to $^{32}$P-labeled cDNA prepared from genomic RNA, and of these. 13 had inserts of 200 to 2000 bases as determined by agarose gel electrophoresis of supercoiled plasmids, and were further analyzed by restriction enzyme analysis and poly (A) content. The largest clone of 2000 bases, FG5, did not react by Southern blotting to $^{32}$P-labeled oligo(dT), but did cross-hybridize in Southern blot analysis with several other smaller clones that did react strongly with oligo(dT). One of these, J21, a clone of 700 bases, was sequenced in part to determine the primary structure of the extreme 3' end of the genome.

Over 96% of the sequence containing the two complete genes in Chart A was determined either by sequencing both strands or by repeated sequencing of the same strand using different methods of end-labeling. Some of the sequences were derived from subclones of FG5 made from the Pst I restriction sites.

The total sequence of FG5 is set forth in Chart A. Sequences from J21 that overlapped with FG5 were identical to those of FG5 except that the total length of the polyadenylate tail was 15 bases for the J21 clone, and 6 for the FG5 clone.

The entire nucleotide sequence was translated in all possible reading frames and only translation of the virus-sense strand revealed open reading frames of greater than 120 bases that were preceded by a termination codon and contained an appropriate initiator methionine codon. Of these, only the two largest open reading frames were evaluated.

The largest open reading frame codes for the nucleocapsid protein. The largest open reading frame extends from base 353 to base 1498 and predicts a 382-amino acid protein of 43, 426 MW The only TGEV protein described to date that approaches this size is the phosphorylated nucleocapsid protein that measures 46 to 50 kd by SDS-polyacrylamide electrophoresis (D J. Garwes and D H. Pocock. J Virol., 29, pp. 25–34 (1975)).

Starting from the nucleocapsid start signal and going leftward to the end of clone FG5 reveals an open reading frame coding for a protein sharing extensive regions of amino acid homology with the small matrix glycoprotein (M or El) of the mouse hepatitis virus A59 except for a 12-base intergenic sequence (J Armstrong et al., Nature, 308, pp. 751–52 (1984)).

A second open reading frame to the 3' side of the nucleocapsid protein gene encodes a protein of 9101 MW that is hydrophobic at both ends. An open reading frame beginning at base 1507 and extending through base 1740 encodes a 78 amino acid protein of 9101 MW.

Example 2

Nucleotide Sequence of the TGEV M Protein Gene Cells and Virus

The Purdue strain of TGEV was grown on swine testicle (ST) cells as previously described (Example 1 -Kapke and Brian. supra). cDNA Cloning of TGEV Genomic RNA cDNA cloning was done according to the method of U. Gubler and B.J. Hoffman, supra, essentially as described in Example 1 and Kapke and Brian, supra, except that the synthetic oligonucleotide 5' TTA-GAAGTTTAGTTA 3' was used as a primer for first-strand cDNA synthesis. The primer was synthesized by the phosphoramadite method and was purified by polyacrylamide gel electrophoresis. Clones were selected by colony hybridization to random-primed cDNA prepared from size-selected genomic RNA (Example 1, Kapke and Brian, supra). Clones were initially mapped by a matrix cross-hybridization method using purified inserts that were labeled by nick-translation.

DNA Sequencing and Sequence Analyses

DNA sequencing and sequence analyses were done as previously described (Example 1, Kapke and Brian, supra).

Results

Six clones designated C4, F5, E2, FT36, FT35, and FT43 were sequenced in part to extend the TGEV genomic sequence that was known from clones FG5 and J21 (Example 1 and Kapke and Brian. supra). As shown in Example 1, clone FG5 maps at the extreme 3' end of the genome and contains the sequence for the hydrophobic protein gene, the N gene and part of the M gene. Identification of the third open reading frame as the M gene sequence was based on regions of extensive amino acid homology with the M proteins of MHV and IBV. Sequencing Strategy Used to Derive the TGEV M Gene Sequence cDNA clones FG5, C4, F5, E2, FT36, and FT35 were cloned into the Pst I site of vector pUC9 and were all found to be in the same orientation with respect to the virus genomic RNA. GT 43 was likewise cloned but was found to be in the opposite orientation.

The molecular weight of the glycosylated M protein has been estimated to be approximately 29 Kd to 30 Kd (Brian et al., supra; Garwes and Pocock, supra; Wesley and Woods, supra). We therefore anticipated that we would be able to deduce from the gene sequence a molecular weight of 29 Kd or less for the unglycosylated protein The extended sequence of what we identified earlier as part of the open reading frame for the M gene (Example 1 and Kapke and Brian, supra) has not yielded an unequivocal demarcation for the amino terminus of the M protein. The nucleotide sequence derived from the 5' end of clone FT36 yields a continuous open reading frame beginning at base position 56 and continuing through the postulated carboxy terminus of the M protein identified as base number 922 in Chart B. A protein produced by this open reading frame would contain 289 amino acids and have a molecular weight of greater than 32 Kd. Although possible, it is unlikely that this polypeptide represents the species identified earlier in protein analyses because of its large size. It is likely that there is, in fact, an open reading frame that is larger than necessary in the genome, but a message of the proper size for the M protein is generated by a transcriptional initiation signal.

The most probable site for initiation of transcription of the M message is suggested by the sequence CTAAAC beginning at base 128 in Chart B, which may be part of a conserved intergenic sequence in the TGEV genome. It is found in total and again in part between the M and N genes beginning at base 926 in Chart B. and also between the N and hypothetical hydrophobic protein genes (Chart A, Kapke and Brian, supra). It is also part of the intergenic sequence found in the MHV genome (Budzilowicz et al., supra). If CTAAAC is an intergenic sequence that directs leader-primed synthesis and thereby defines the start of the M transcript for TGEV, then the M protein coding sequence could start with the first available methionine which begins at base 137 in Chart B. Using this as the amino terminus, the deduced M protein is comprised of 262 amino acids and has a molecular weight of 29,544. The protein is moderately hydrophobic with 44% of its amino acids being hydrophobic, and is basic since it carries a net charge of +7 at neutral pH.

Example 3

Diagnosis of TGEV Infections Using Cloned cDNA Probes

In this example we describe the use of cloned TGEV cDNA as hybridization probes that serve to identify TGEV infections in baby pigs. The TGEV probes detected as little as 25 pg of homologous RNA on nitrocellulose, but no signal was observed for heterologous RNA even when amounts of 10 ng per dot were used Viral RNA was detectable in specimens prepared directly from cell cultures or from fecal material. Results of electron microscopy, virus isolation and dot blot hybridization analyses were compared on fecal swabs taken from a litter of piglets experimentally infected with TGEV. Cells and viruses TGEV, Purdue strain, bovine enteric coronavirus. Mebus strain (BCV), human respiratory coronavirus, strain OC43 (HCV OC43), mousehepatitis virus, A59 strain (MHV), vesicular stomatitis virus, Indiana strain (VSV), and Newcastle disease virus, Lasota strain (NDV), were grown as previously described (D A. Brian et al., J. Virol., 34, pp. 410-15 (1980); D.E. Dennis and D.A. Brian, J. Virol., 42, pp. 153–64 (1982); W. Lapps and D.A. Brian. Arch. Virol., 86. pp. 101–08 (1985)). Canine coronavirus (CCV) and feline infectious peritonitis virus (FIPV) were grown on a fetal cat cell line (established by R. Woods), porcine hemagglutinating encephalomyelitis virus, strain 67N (HEV), was grown on the human rectal tumor cell line HRT-18 (Lapps and Brian, supra), and human respiratory coronavirus, strain 229E (HCV 229E). was grown on WI-38 cells (American Type Culture Collection).

Preparation of Virion RNA for Nitrocellulose Binding

Methods used for infection of cells, virus purification and virion RNA extraction have been described previously (Brian et al, supra; Lapps and Brian, supra). For these studies, virus (BCV, TGEV, or MHV) was purified from clarified supernatant fluids by pelleting through a barrier of 32% sucrose (wt/wt) made up in TMEN (100 mM Tris maleate [pH 6.0]—100 mM NaCl-1 mM EDTA). Virion RNA was extracted using the proteinase K-SDS-phenol method (Brian et al., supra). RNA was dissolved in water and spectrophotometrically quantitated assuming 1 $A_{254}$ unit in 1 ml is equal to 42 $\mu g$ RNA. RNA was handled at all times in baked or autoclaved siliconized containers and prepared in solutions made from diethylpyrocarbonate-treated water.

For nitrocellulose binding, purified virion RNA, cell culture-grown virus, or fecal specimens were treated essentially as described by B. White and F. Bancroft, J. Biol. Chem., 257, pp. 8569–72 (1982) for the binding of cytoplasmic RNA Preliminary experiments demonstrated that Nonidet-P40 (NP-40) (Shell) enhanced the binding of RNA to nitrocellulose, even in its purified form RNA was therefore dissolved and diluted in TE buffer (10 mM Tris [pH 7.0]—1 mM EDTA) and each sample was made 0.5% NP-40 by adding an equal volume of 1% NP-40 in TE buffer. To each NP-40-treated sample was added an equal volume of a freshly prepred solution of two parts 37% (w/W) formaldehyde and three parts 20×SSC, and the mixture was heated at 60° for 15 minutes just prior to loading onto nitrocellulose. RNA dilutions were made in siliconized 96-well microtiter plates.

Preparation of Cell Culture-Grown Virus for Nitrocellulose Binding

Cells were infected at a multiplicity of approximately 1 PFU per cell and cell culture fluids were harvested at 17,48, and 10 hours post-infection respectively for TGEV, BCV, and MHV Culture fluids were clarified by centrifugation at 2,000 ×g for 10 minutes and stored at 80° C. until use. Virus dilutions were made in TE buffer and virus was lysed by the addition of an equal volume 1% NP40 in TE buffer Samples were incubated for 10 minutes at 0° C., treated with an equal volume of formaldehyde-20×SSC solution, and heated at 60° C. for 15 minutes prior to loading onto nitrocellulose.

Preparation of Fecal Specimens for Nitrocellulose Binding

Individuals in a litter of twelve 3-day-old pigs were given 5 ml of inoculum by stomach tube of a given dilution of TGEV stock. Virus stock had a titer of $7.1 \times 10^6$ PFU/ml and was prepared from small intestinal contents of a piglet that had been infected with TGEV, Miller strain. Virus used for inoculating the piglet, from which stock virus was prepared, had undergone 11 passages in gnotobiotic pigs subsequent to plaque purification in cell cultures (G.T. Frederick et al., Am. J. Vet. Res., 37, pp. 165–69 (1976)). Pigs 1 and 2 were inoculated with $10^{-1}$ dilution 3 and 4 with $10^{-2}$ dilution, 5 and 6 with $10^{-3}$ dilution 7 and 8 with $10^{-4}$ dilution, 9 and 10 with $10^{-5}$ dilution, and 11 and 12 with $10^{-6}$ dilution of virus stock. Fecal specimens were taken with dry cotton swabs and stored at $-50°$ C. until used. To prepare samples. 0.75 ml of sterile Earle's Balanced Salt Solution (EBSS) was added to the tube containing the swab and after vortexing briefly, the fluid was removed and clarified by microfuge centrifugation for 30 sec. Clarified fluid was either treated for nitrocellulose binding directly (termed "undiluted"), or after diluting 1:10 in TE buffer. Virus was lysed and treated for nitrocellulose binding as described above for cell culture grown virus.

Binding of RNA-Containing Samples to Nitrocellulose

Nitrocellulose (BA85; Schleicher and Schuell, Inc.) was soaked in DEPC-treated water and equilibrated with 20×SSC before application of samples. Nitrocellulose was supported by two sheets of blotting paper in a 96-hole dot-blot apparatus (Minifold, Schleicher and Schuell, Inc.). 100 μl samples, prepared as described above, were applied per well Samples of purified RNA were allowed to set for 30 seconds before light suction was applied. With all other samples, strong suction was applied immediately. Treated nitrocellulose sheets were air dried and baked at 75° C. for 90 minutes in vacuum oven to fix the RNA (P.S. Thomas, Proc. Natl. Acad. Sci., 77, pp. 5205–09 (1980)).

Preparation of Cloned cDNA Probes and Molecular Hybridization cDNA clones of TGEV representing the 3′ end of the genome have been prepared and characterized (Examples 1 and 2 and Kapke and Brian, supra). Clone pTGEV-FG5 from Example 1, which represents the first (3′) 2.0 Kb sequence of the 20 Kb TGEV genome, was selected for use in this study. This region includes the complete 3′ noncoding region, the nucleocapsid (N) protein gene and a large portion of the matrix (M) protein gene, as determined by an analysis of the primary structure of these sequences (Examples 1 and 2, Kapke and Brian, supra). cDNA was cloned into plasmid PUC9 using E. coli strain JMI103 as the host. Insert-containing plasmid was obtained from cultured bacteria using lysozyme and alkali and purified on CsCl gradients (T.E. Maniatis et al., supra). Insert DNA was cleaved from plasmid using restriction endonucleases Bam HI and Hind III (Pharmacia). The TGEV clone FG5 yielded two fragments of 1.3 and 0.7 Kb because of an internal Hind III cutting site. Fragments were recovered by preparative electrophoresis in 1% agarose gels and electroelution (Maniatis et al., supra). Purified inserts were labeled to specific activities of $1.4 \times 10^8$ cpm per ug by nick-translation with $^{32}P$ dCTP (P.W. Rigby et al, J. Mol. Biol., 113, pp. 237–51 (1977)). Before they were used for hybridization, probes were denatured by heating for five minutes at 100° C. followed by quick-cooling on ice. Hybridization was carried out essentially as described by P S. Thomas. Proc. Natl. Acad. Sci., 77, pp. 5205–09 (1980). but without dextran sulfate Blots were incubated (prehybridized) for 4 hours at 42° C. in sealed plastic bags containing a solution (1 ml/cm$^2$) of 50% formamide-5×SSC-50 mM Na$_2$HPO$_4$ (pH 6.5)—0.2% SDS-1X Denhardt's solution (0.02% bovine serum albumin-0.02% polyvinylpyrrolidone-0.02% Ficoll)-250 ug sheared, denatured salmon sperm DNA per ml. Fluids were removed and fresh solution (1 ml/cm$^2$) and denatured cDNA probe (10$^6$ cpm/cm$^2$) were added to the bag. The bag was sealed, incubated at 42° C. for 16–24 hours, and the nitrocellulose washed four times with 2X SSC-0.1% SDS for five minutes at room temperature, then twice with 0.1 X SSC.0.1% SDS for 15 minutes at 50° C. Dried blots were exposed to Kodak AR X-ray film at $-70°$ C. with intensifying screen for 24–48 hours.

Immunofluorescence Testing

Immunofluorescence testing was performed essentially as described by L.N.D. Potgieter and P.L. Aldridge. Am. J. Vet. Res., 38, pp. 1341–43 (1977). Cells were scraped from the flask, washed and suspended in phosphate-buffered saline, spread onto glass slides, dried, fixed with acetone, incubated with TGEV-positive (hyperimmune) pig serum or preimmune serum, and stained with fluorescent-labeled rabbit anti-swine IgG (Miles Laboratories).

Electron Microscopy

Fecal samples were prepared for electron microscopy essentially as described by J.D. Almeida, Yale J. Biol Med., 53 pp. 5–18 (1980). A portion of the clarified resuspended fecal material was centrifuged at 15,000 ×g for 10 min and the pellet was resuspended in a minimal amount of deionized water One volume of resuspended pellet was mixed with 9 volumes of deionized water and one volume of 4.0% phosphotungstic acid (neutralized to pH 7.0), and sprayed onto a formvar-carbon-coated grid using a glass nebulizer.

Specificity and Sensitivity of Cloned cDNA Probes in Dot Blot Hybridization Reactions To determine the specificity and sensitivity of the probe for its TGEV RNA, RNA extracted from purified TGEV, BCV, or yeast transfer RNA was applied to nitrocellulose in amounts ranging from 10 pg to 10 ng per dot, and tested for hybridization with the TGEV probe. The probe bound specifically to its homologous RNA and no reactivity with heterologous RNA was observed. Furthermore, the probe was able to detect as little as 25 pg of homologous RNA per dot, the amount of RNA from $2 \times 10^6$ virions assuming a genome size of $7 \times 10^6$ daltons for TGEV (Brian et al., supra; Lapps and Brian, supra). Dot blots of 10 ng of MHV, NDV, and VSV RNA were also tested with the probe and no detectable binding was observed.

Detection of RNA by Dot Blot Hybridization in Virus Prepared Directly from Cell Culture Fluids Cell culture fluids from virus-infected cells were used firstly to establish a procedure for detecting virus from body fluids and secondly to examine the usefulness of the TGEV probe for identifying other coronaviruses. For the first purpose, a series of ten-fold dilutions of clarified cell culture fluids from TGEV., BCV., and MHV-infected cells were denatured and applied to nitrocellulose. The probe hybridized in a specific manner to its parental RNAs except for the lowest dilutions of virus at which some TGEV probe bound to BCV but not to MHV. The apparent hybridization at low dilutions of virus is probably artifactual since there was no reciprocal hybridization between a BCV probe and TGEV. In other blotting experiments, probe failed to hybridize to VSV from cell culture fluids. This further established the specificity of the probe.

To examine the reactivity of the TGEV probe with other corona-viruses, various cell culture-grown coronaviruses were applied to nitrocellulose in the same manner, except for only a limited number of dilutions. In general, the probe did not react with viruses belonging to the unrelated antigenic subgroup, nor did they identify all the viruses antigenically related to the clone's parent. The TGEV probe hybridized with CCV and FIPV, but not with HCV 229E. These differences undoubtedly reflect evolutionary distances between the viruses and illustrates the potential usefulness of hybridization probes for the eventual identification of coronavirus subgroups. Detection of TGEV RNA in Virus from Fecal Samples and Comparison of Dot Blot Hybridization with Other Diagnostic Methods To establish the usefulness of the dot blot procedure for identifying coronaviruses in fecal samples, a litter of 12 piglets was experimentally infected with TGEV as described above and fecal swabs were taken at 0, 18, 30, 44, 90. and 114 hours post-infection from each survivor. Swabs were processed for dot blot hybridization against the TGEV probe, and swabs from 6 of the animals were additionally processed for diagnosis by electron microscopy and infectivity (as determined by cytopathic effect and immunofluorescence).

From these studies the following points emerge. (1) The abundance of TGEV particles in the feces of infected animals is more than adequate for detection by the dot blot hybridization test. Since the amount of feces absorbed by the cotton swab is approximately 0.5 ml, the volume of fecal equivalents adsorbed in one dot of an "undiluted" sample is approximately 10 ul. A dot of fecal sample containing 25 pg RNA would therefore be equivalent to $2 \times 10^8$ virions/ml of feces if the sample is "undiluted," or $2 \times 10^9$ virions-/ml if the sample is diluted 1:10. Dots having 50 ug virion RNA or more, as observed at peak times for animals 3, 4, 5, 11, and 12 would therefore be equivalent to fecal concentrations of at least $4 \times 10^{11}$ and $4 \times 10^{12}$ virions/ml for samples that are "undiluted" or diluted 1:10 respectively. (2) The time of virus appearance in feces did not reflect the inoculum size. Animals receiving 35 pfu (11 and 12) began shedding virus earlier than animals receiving a far larger inoculum (e.g., animal 1 that received $35 \times 10^5$ pfu and animal 3 that received $35 \times 10^4$ pfu). In no animal was viral RNA detectable until greater than 18 hours after infection. Four piglets (numbers 5, 6, 11, and 12) did not survive to 114 hours postinfection and, for these, a 90 hour sample was the last one taken. (3) Abundance patterns in two of the animals (2 and 4) suggest that there may be both a rapid onset and rapid decline in the number of excreted viruses during the three-day course of infection, although a wide variation in sampling quantities that could also explain this pattern cannot be ruled out. For these animals, virus appeared to be most abundant at 30 h postinfection and quantities decreased from 44 h through 114 h postinfection. (4) The high viscosity of some undiluted samples interfered with RNA adherence to the nitrocellulose. This was seen for piglets 1, 2, 4, 7, 8, and 12 at the 90 h timepoint and for piglets 1, 2, 4, 7, 9, and 10 at the 144 h timepoint. These samples appeared to peel off the nitrocellulose during processing. This problem was not observed with the diluted samples.

When comparison was made between the dot blot hybridization test, electron microcoscopy and virus isolation tests of diagnosis on 6 of the animals, the best correlation was found with the virus isolation test as confirmed by immunofluorescence. In only one case, animal 5 at 90 h postinfection, did the virus isolation test and hybridization tests disagree. In this case the sample was taken during the declining stages of infection, a time when the number of viable viruses may be low relative to the total number, thus yielding a positive test by hybridization and a negative test by infectivity. Less correlation was observed between the dot blot hybridization test and electron microscopy. Generally virus was detected sooner by electron microscopy than by virus isolation and dot blot hybridization, however, the particles observed may have only been coronavirus, like particles of the type commonly observed in the diseased gut, and not true coronaviruses.

The availability of the gene sequences of the present invention permits direct manipulation of the genes and gene sequences which allows modifications of the regulation of expression and/or the structure of the protein encoded by the gene or a fragment thereof. Knowledge of these gene sequences also allows one to clone the corresponding gene, or fragment thereof, from any strain of TGEV using the known sequence as a hybridization probe, and to express the entire protein or fragment thereof by recombinant techniques generally known in the art.

Knowledge of these gene sequences enabled us to deduce the amino acid sequence of the corresponding polypeptides (Charts A and B). As a result, fragments of these polypeptides having TGEV immunogenicity can be produced by standard methods of protein synthesis or recombinant DNA techniques.

The primary structures (sequences) of the genes coding, inter alia, for the M. N, and P proteins from TGEV also are set forth in Charts A and B.

The excised gene or fragments thereof can be ligated to various cloning vehicles or vectors for use in transforming a host cell. The vectors preferably contain DNA sequences to initiate, control and terminate transcription and translation (which together comprise expression) of the TGEV polypeptide genes and are, therefore, operatively linked thereto. These "expression control sequences" are preferably compatible with the host cell to be transformed. When the host cell is a higher animal cell, e.g., a mammalian cell, the naturally occurring expression control sequences of the polypeptide genes can be employed alone or together with heterologous expression control sequences. Heterologous sequences may also be employed alone. The vectors additionally preferably contain a marker gene (e.g., antibiotic resistance) to provide a phenotypic trait for selection of transformed host cells. Additionally a replicating vector will contain a replicon.

Typical vectors are plasmids, phages, and viruses that infect animal cells. In essence, one can use any DNA sequence that is capable of transforming a host cell.

The term host cell as used herein means a cell capable of being transformed with the DNA sequence coding for a polypeptide displaying TGEV polypeptide antigenicity. Preferably, the host cell is capable of expressing the TGEV polypeptide or fragments thereof. The host cell can be procaryotic or eucaryotic. Illustrative procaryotic cells are bacteria such as *E. coli, B. subtilis, Pseudomonas, and B. stearothermophilus.* Illustrative eucaryotic cells are yeast or higher animal cells such as cells of insect, plant or mammalian origin. Mammalian cell systems often will be in the form of monolayers of cells although mammalian cell suspensions may also be used. Mammalian cell lines include, for example, VERO and HeLa cells, Chinese hamster ovary (CHO) cell lines, WI38, BHK, COS-7 or MDCK cell lines. Insect cell lines include the Sf9 line of Spodoptera frugipe-rda (ATCC CRL1711) A summary of some available eucaryotic plasmids, host cells and methods for employing them for cloning and expressing TGEV polypeptides can be found in K Esser, et al., Plasmids of Eukaryotes (Fundamentals and Applications), Springer-Verlag (1986) which is incorporated herein by reference.

As indicated above, the vector, e.g., a plasmid, which is used to transform the host cell preferably contains compatible expression control sequences for expression of the TGEV polypeptide gene or fragments thereof. The expression control sequences are, therefore, operatively linked to the gene or fragment When the host cells are bacteria, illustrative useful expression control sequences include the trp promoter and operator (Goeddel. et al., Nucl. Acids Res., 8, 4057 (1980)); the lac promoter and operator (Chang. et al., Nature, 275, 615 (1978)); the outer membrane protein promoter (EMBO J, 1, 771-775 (1982)); the bacteriophage λ promoters and operators (Nucl. Acids Res., 11, 4677-4688 (1983)); the α-amylase (*B. subtilis*) promoter and oparator, termination sequences and other expression enhancement and control sequences compatible with the selected host cell. When the host cell is yeast, illustrative useful expression control sequences include. e g., o-mating factor. For insect cells the polyhedrin promoter of baculoviruses can be used (Mol. Cell. Biol., 3, pp. 2156-65 (1983)). When the host cell is of insect or mammalian origin illustrative useful expression control sequences include, e.g., the SV-40 promoter (Science, 222, 524-527 (1983)) or, e.g., the metallothionein promoter (Nature, 296, 39-42 (1982)) or a heat shock promoter (Voellmy, et al., Proc. Natl. Acad. Sci USA, 82, pp. 4949-53 (1985)). As noted above, when the host cell is mammalian one may use the expression control sequences for the TGEV polypeptide gene but preferably in combination with heterologous expression control sequences.

The plasmid or replicating or integrating DNA material containing the expression control sequences is cleaved using restriction enzymes, adjusted in size as necessary or desirable, and ligated with the TGEV polypeptide gene or fragments thereof by means well known in the art. When yeast or higher animal host cells are employed, polyadenylation or terminator sequences from known yeast or mammalian genes may be incorporated into the vector. For example, the bovine growth hormone polyadenylation sequence may be used as set forth in European publication number 0 093 619 which is incorporated herein by reference. Additionally gene sequences to control replication of the host cell may be incorporated into the vector.

The host cells are competent or rendered competent for transformation by various means. When bacterial cells are the host cells they can be rendered competent by treatment with salts, typically a calcium salt, as generally described by Cohen, PNAS, 69, 2110 (1972). A yeast host cell generally is rendered competent by removal of its cell wall or by other means such as ionic treatment (J. Bacteriol., 153, 163-168 (1983)). There are several well-known methods of introducing DNA into animal cells including. e.g., calcium phosphate precipitation, fusion of the recipient cells with bacterial protoplasts containing the DNA. treatment of the recipient cells with liposomes containing the DNA, and microinjection of the DNA directly into the cells.

The transformed cells are grown up by means well known in the art (Molecular Cloning. Maniatis, T., et al.. Cold Spring Harbor Laboratory, (1982); Biochemical Methods In Cell Culture And Virology, Kuchler, R. J., Dowden, Hutchinson and Ross. Inc , (1977); Methods In Yeast Genetics. Sherman, F., et al., Cold Spring Harbor Laboratory, (1982)) and the expressed TGEV polypeptide or fragment thereof is harvested from the cell medium in those systems where the protein is excreted from the host cell, or from the cell suspension after disruption of the host cell system by. e.g., mechanical or enzymatic means which are well known in the art.

There are several convenient methods that can be used to express the TGEV genes of the present invention. For example, the M and P genes can be inserted in the pseudorabies virus (PRV) genome as set forth in the example relating to tissue plasminogen activator in PCT application PCT/US86/01322, which is incorporated herein by reference. The TGEV gene of interest is cloned downstream from the gX promoter and flanked with the BamHI 7 fragment. This plasmid is co-transfected with the PRV having a deletion for the gX gene and thymidine kinase deficient recombinants are selected. The recombinant PRV so produced, comprising the TGEV gene of interest, expresses the TGEV polypeptide encoded thereby.

The TGEV genes of interest can also be inserted in the vaccinia virus according to the method of Mackett. et al, in *DNA Cloning, Volume II, A Practical Approach,* D.M. Glover, d. (1985), with the improvement comprising using PSCII as the plasmid vector as described by Chakrabarty et al. Mol. Cell Biol., 5, 3403-09 (1985). The method is essentially described in PCT application PCT/US86-01761, which is incorporated herein by reference, except that the pSC11 vector is substituted for pGS20.

As noted above, the amino acid sequences of the TGEV polypeptides as deduced from the gene structures are set forth in Charts A and B. Polypeptides displaying TGEV polypeptide antigenicity include the sequences set forth in Charts A and B and any portions of the polypeptide sequences which are capable of eliciting an immune response in an animal. e.g., a mammal, which has been injected with the polypeptide sequence and also immunogenically functional analogs of the polypeptides.

As indicated hereinabove the entire gene coding for the TGEV polypeptide can be employed in constructing the vectors and transforming the host cells to express the TGEV polypeptide, or fragments of the gene coding for the TGEV polypeptide can be employed, whereby the resulting host cell will express polypeptides displaying TGEV antigenicity. Any fragment of the TGEV polypeptide gene can be employed which results in the expression of a polypeptide which is an immunogenic fragment of the TGEV polypeptide or an analog thereof. As is well known in the art, the degeneracy of the genetic code permits easy substitution of base pairs to produce functionally equivalent genes and fragments thereof encoding polypeptides displaying TGEV polypeptide antigenicity. These functional equivalents also are included within the scope of the invention.

Additionally, it is considered that there may be only certain fragments of the entire amino acid sequence of the TGEV polypeptides, together with their spacing and interrelationship with other fragments which are primarily for the TGEV immunogenicity. Thus, except for those critical fragments which are primarily responsible for the TGEV immunogenicity, a further interchange of amino acids or other materials in the TGEV gene sequences is acceptable.

A vaccine prepared utilizing a polypeptide of the instant invention or an immunogenic fragment thereof can consist of fixed host cells, a host cell extract, or a partially or completely purified TGEV polypeptide preparation from the host cells or produced by chemical synthesis. The TGEV polypeptide immunogen prepared in accordance with the present invention is preferably free of TGEV virus. Thus, the vaccine immunogen of the invention is composed substantially entirely of the desired immunogenic TGEV polypeptide and/or other TGEV polypeptides displaying TGEV antigenicity.

The immunogen can be prepared in vaccine dose form by well-known procedures. The vaccine can be administered intramuscularly, subcutaneously or intranasally. For parenteral administration, such as intramuscular injection, the immunogen may be combined with a suitable carrier, for example, it may be administered in water, saline or buffered vehicles with or without various adjuvants or immunomodulating agents including aluminum hydroxide, aluminum phosphate, aluminum potassium sulfate (alum), beryllium sulfate, silica, kaolin, carbon, water-in-oil emulsions, oil-in-water emulsions, muramyl dipeptide. bacterial endotoxin, lipid X, Corynebacterium parvum (Propionobacterium acnes). Bordetella pertussis, polyribonucleotides, sodium alginate, lanolin, lysolecithin, vitamin A, saponin, liposomes, levamisole, DEAE-dextran, blocked copolymers or other synthetic adjuvants Such adjuvants are available commercially from various sources, for example, Merck Adjuvant 65 (Merck and Company, Inc., Rahway, N.J.). Another suitable adjuvant is Freund's Incomplete Adjuvant (Difco Laboratories, Detroit, Mich.).

The proportion of immunogen and adjuvant can be varied over a broad range so long as both are present in effective amounts. For example, aluminum hydroxide can be present in an amount of about 0.5% of the vaccine mixture ($Al_2O_3$ basis). On a per dose basis, the concentration of the immunogen can range from about 1.0 $\mu$g to about 100 mg per pig. A preferable range is from about 100 $\mu$g to about 3.0 mg per pig. A suitable dose size is about 1–10 ml, preferably about 1.0 ml. Accordingly, a dose for intramuscular injection, for example, would comprise 1 ml containing 1.0 mg of immunogen in admixture with 0.5% aluminum hydroxide. Comparable dose forms can also be prepared for parenteral administration to baby pigs, but the amount of immunogen per dose will be smaller, for example, about 0.25 to about 1.0 mg per dose.

For vaccination of sows, a two dose regimen can be used The first dose can be given from about several months to about 5 to 7 weeks prior to farrowing. The second dose of the vaccine then should be administered some weeks after the first dose, for example, about 2 to 4 weeks later, and vaccine can then be administered up to, but prior to, farrowing. Alternatively, the vaccine can be administered as a single 2 ml dose, for example, at about 5 to 7 weeks prior to farrowing. However, a 2 dose regimen is considered preferable for the most effective immunization of the baby pigs. Semi-annual revaccination is recommended for breeding animals. Boars may be revaccinated at any time. Also, sows can be revaccinated before breeding. Piglets born to unvaccinated sows may be vaccinated at about 3–10 days, again at 4–6 months and yearly or preferably semi-annually thereafter.

The vaccine may also be combined with other vaccines for other diseases to produce multivalent vaccines It may also be combined with other medicaments, for example, antibiotics. A pharmaceutically effective amount of the vaccine can be employed with a pharmaceutically acceptable carrier or diluent to vaccinate animals such as swine, cattle, sheep, goats, and other mammals.

Other vaccines may be prepared according to methods well known to those skilled in the art as set forth, for example, in I Tizard. An Introduction to Veterinary Immunology. 2nd ed (1982). which is incorporated herein by reference.

Chart A.

```
                        30                              60
CGGGGGGGGGGGGGGGGGGTCTTTGCGTTAGTGCATTAGGAAGAAGCTATGTGCTTCCTCT
       L   C   V   S   A   L   G   R   S   Y   V   L   P   L 90                              120
CGAAGGTGTGCCAACTGGTGTCACTCTAACTTTGCTTTCAGGGAATTTGTACGCTGAAGG
   E   G   V   P   T   G   V   T   L   T   L   L   S   G   N   L   Y   A   E   G 150                             180
GTTCAAAATTGCAGGTGGTATGAACATCGACAATTTACCAAAATACGTAATGGTTGCATT
   F   K   I   A   G   G   M   N   I   D   N   L   P   K   Y   V   M   V   A   L
```

-continued

Chart A.

```
                    210                                    240
ACCTAGCAGGACTATTGTCTACACACTTTGTTGGCAAGAAGTTGAAAGCAAGTAGTGCGAC
  P  S  R  T  I  V  Y  T  L  V  G  K  K  L  K  A  S  S  A  T 270                                    300
TGGATGGGCTTACTATGTAAAATCTAAAGCTGGTGATTACTCAACAGAGGCAAGAACTGA
  G  W  A  Y  Y  V  K  S  K  A  G  D  Y  S  T  E  A  R  T  D 330                                    360
TAATTTGAGTGAGCAAGAAAAATTATTACATATGGTATAACTAAACTTTCTAAATGGCCAA
  N  L  S  E  Q  E  K  L  L  H  M  V                 M  A  N 390                                    420
CCAGGGACAACGTGTCAGTTGGGGAGATGAATCTACCAAAACACGTGGTCGTTCCAATTC
  Q  G  Q  R  V  S  W  G  D  E  S  T  K  T  R  G  R  S  N  S 450                                    480
CCGTGGTCGGAAGAATAATAACATACCTCTTTCATTCTTCAACCCCATAACCCTCCAACA
  R  G  R  K  N  N  I  P  L  S  F  F  N  P  I  T  L  Q  Q 510                                    540
AGGTTCAAAATTTTGGAACTTATGTCCGAGAGACTTTGTACCCAAAGGAATAGGTAACAG
  G  S  K  F  W  N  L  C  P  R  D  F  V  P  K  G  I  G  N  R 570                                    600
GGATCAACAGATTGGTTATTGGAATAGACAAACTCGCTATCGCATGGTGAAGGGCCAACG
  D  Q  Q  I  G  Y  W  N  R  Q  T  R  Y  R  M  V  K  G  Q  R 630                                    660
TAAAGAGCTTCCTGAAAGGTGGTTCTTCTACTACTTAGGTACTGGACCTCATGCAGATGC
  K  E  L  P  E  R  W  F  F  Y  Y  L  G  T  G  P  H  A  D  A 690                                    720
CAAATTTAAAGATAAATTAGATGGAGTTGTCTGGGTTGCCAAGGATGGTGCCATGAACAA
  K  F  K  D  K  L  D  G  V  V  W  V  A  K  D  G  A  M  N  K 750                                    780
ACCAACCACGCTTGGTAGTCGTGGTGCTAATAATGAATCCAAAGCTTTGAAATTCGATGG
  P  T  T  L  G  S  R  G  A  N  N  E  S  K  A  L  K  F  D  G 810                                    840
TAAAGTGCCAGGCGAATTTCAACTTGAAGTTAATCAATCAAGAGACAATTCAAGGTCACG
  K  V  P  G  E  F  Q  L  E  V  N  Q  S  R  D  N  S  R  S  R 870                                    900
CTCTCAATCTAGATCTCGGTCTAGAAATAGATCTCAATCTAGAGGCAGGCAACAATTCAA
  S  Q  S  R  S  R  S  R  N  R  S  Q  S  R  G  R  Q  Q  F  N 930                                    960
TAACAAGAAGGATGACAGTGTAGAACAAGCTGTTCTTGCCGCACTTAAAAAGTTAGGTGT
  N  K  K  D  D  S  V  E  Q  A  V  L  A  A  L  K  K  L  G  V 990                                   1020
TGACACAGAAAAACAACAGCAACGCTCTCGTTCTAAATCTAAAGAACGTAGTAACTCTAA
  D  T  E  K  Q  Q  Q  R  S  R  S  K  S  K  E  R  S  N  S  K 1050                                  1080
GACAAGAGATACTACACCTAAGAATGAAAACAACACACCTCGAAGAGAACTGCAGGTAA
  T  R  D  T  T  P  K  N  E  N  K  H  T  S  K  R  T  A  G  K 1110                                  1140
AGGTGATGTGACAAGATTTTATGGAGCTAGAAGCAGTTCAGCCAATTTTGGTGACACTGA
  G  D  V  T  R  F  Y  G  A  R  S  S  A  N  F  G  D  T  D 1170                                  1200
CCTCGTTGCCAATGGGAGCAGTGCCAAGCATTACCCACAACTGGCTGAATGTGTTCCATC
  L  V  A  N  G  S  S  A  K  H  Y  P  Q  L  A  E  C  V  P  S 1230                                  1260
TGTGTCTAGCATTCTGTTTGGAAGCTATTGGACTTCAAAGGAAGATGGCGACCAGATAGA
  V  S  S  I  L  F  G  S  Y  W  T  S  K  E  D  G  D  Q  I  E 1290                                  1320
AGTCACGTTCACACACAAATACCACTTGCCAAAGGATGATCCTAAGACTGGACAATTCCT
  V  T  F  T  H  K  Y  H  L  P  K  K  D  P  K  T  G  Q  F  L 1350                                  1380
TCAGCAGATTAATGCCTATGCTCGTCCATCAGAAGTGGCAAAAGAACAGAGAAAAAGAAA
  Q  Q  I  N  A  Y  A  R  P  S  E  V  A  K  E  Q  R  K  R  K
```

Chart A.

```
                                                              1410                                           1440
ATCTCGTTCTAAATCTGCAGAAAGGTCAGAGCAAGATGTGGTACCTGATGCATTAATAGA
 S  R  S  K  S  A  E  R  S  E  Q  D  V  V  P  D  A  L  I  E 1470                                          1500
AAATTATACAGATGTGTTTGATGACACACAGGTTGAGATAATTGATGAGGTAACGAACTA
 N  Y  T  D  V  F  D  D  T  Q  V  E  I  I  D  E  V  T  N 1530                                          1560
AACGAGATGCTCGTCTTCCTCCATGCTGTATTTATTACAGTTTTAATCTTACTACTAATT
 M  L  V  F  L  H  A  V  F  I  T  V  L  I  L  L  L  I 1590                                          1620
GGTAGACTCCAATTATTAGAAAGACTATTACTTGATCACTCTTTCAATCTTAAAACTGTC
 G  R  L  Q  L  L  E  R  L  L  L  D  H  S  F  N  L  K  T  V 1650                                          1680
AATGACTTTAATATCTTATATAGGAGTTTAGCAGAAACCAGATTACTAAAAGTGGTGCTT
 N  D  F  N  I  L  Y  R  S  L  A  E  T  R  L  L  K  V  V  L 1710                                          1740
CGAGTAATCTTTCTAGTCTTACTAGGATTTTGCTGCTACAGATTGTTAGTCACATTAGTG
 R  V  I  F  L  V  L  L  G  F  C  C  Y  R  L  L  V  T  L  V 1770                                          1800
TAAGGCAACCCGATGTCTAAAACTGGTTTTTCCGAGGAATTACTGGTCATCGCGCTGTCT 1830                                          1860
ACTCTTGTACAGAATGGTAAGCACGTGTAATAGGAGGTACAAGCAACCCTATTGCATATT 1890                                          1920
AGGAAGTTTAGATTTGATTTGGCAATGCTAGATTTAGTAATTTAGAGAAGTTTAAAGATC 1950                                          1980
CGCTACGACGAGCCAACAATGGAAGAGCTAACGTCTGGATCTAGTGATTGTTTAAAATGT

2010
AAAATTGTTTGAAAATTTTCCTTTTGATAGTGATACAAAAAACCCCCCCCCCCCCC
```

Chart B.

```
                       30                                              60
CTATGCATGGTGTGTTGCAATTTAGCAAGGACAGTTATTATTGTTCCAGCGCAACATGCT
                                                              M  L 90                                           120
TACGATGCCTATAAGAATTTTATGCGAATTAAAGCATACAACCCCGATGGAGCACTCCTT
 T  M  P  I  R  I  L  C  E  L  K  H  T  T  P  M  E  H  S  L 150                                          180
GCTTGAACTAAACAAAATGAAGATTTTGTTAATATTAGCGTGTGTGATTGCATGCGCATG
 L  E  L  N  K  M  K  I  L  L  I  L  A  C  V  I  A  C  A  C 210                                          240
TGGAGAACGCTATTGTGCTATGAAATCCGATACAGATTTGTCATGTCGCAATAGTACAGC
 G  E  R  Y  C  A  M  K  S  D  T  D  L  S  C  R  N  S  T  A 270                                          300
GTCTGATTGTGAGTCATGCTTCAACGGAGGCGATCTTATTTGGCATCTTGCAAACTGGAA
 S  D  C  E  S  C  F  N  G  G  D  L  I  W  H  L  A  N  W  N 330                                          360
CTTCAGCTGGTCTATAATATTGATCGTTTTTATAACTGTGCTACAATATGGAAGACCTCA
 F  S  W  S  I  I  L  I  V  F  I  T  V  L  Q  Y  G  R  P  Q 390                                          410
ATTCAGCTGGTTCGCGTATGGCATTAAAATGCTTATAATGTGGCTATATGGCCCGTTGT
 F  S  W  F  A  Y  G  I  K  M  L  I  M  W  L  L  W  P  V  V 450                                          480
TTTGGCTCTTACGATTTTTAATGCATACTCGGAATACCAAGTGTCCAGATATGTAATGTT
 L  A  L  T  I  F  N  A  Y  S  E  Y  Q  V  S  R  Y  V  M  F 510                                          540
CGGCTTTAGTATTGCAGGTGCAATTGTTACATTTGTACTCTGGATTATGTATTTTGTAAG
 G  F  S  I  A  G  A  I  V  T  F  V  L  W  I  N  Y  F  V  R
```

Chart B.

```
                570                                      600
ATCCATTCAGTTGTACAGAAGGACTAAGTCTTGGTGGTCTTTCAACCCTGAAACTAAAGC
  S  I  Q  L  Y  R  R  T  K  S  W  W  S  F  N  P  E  T  K  A 630                                      660
AATTCTTTGCGTTAGTGCATTAGGAAGAAGCTATGTGCTTCCTCTCGAAGGTGTGCCAAC
  I  L  C  V  S  A  L  G  R  S  Y  V  L  P  L  E  Q  V  P  T 690                                      720
TGGTGTCACTCTAACTTTGCTTCAGGGAATTTGTACGCTGAAGGGTTCAAAATTGCAGG
  G  V  T  L  T  L  L  S  G  N  L  Y  A  E  G  F  K  I  A  G 750                                      780
TGGTATGAACATCGACAATTTACCAAAATACGTTGCATTACCTAGCAGGACTAT
  G  M  M  I  D  M  L  P  K  Y  V  A  L  P  S  R  T  I 810                                      840
TGTCTACACACTTGTTGGCAAGAAGTTGAAAGCAAGTAGTGCGACTGGATGGGCTTACTA
  V  Y  T  L  V  G  K  K  L  K  A  S  S  A  T  G  W  A  Y  Y 870                                      900
TGTAAAATCTAAAGCTGGTGATTACTCAACAGAGGCAAGAACTGATAATTTGAGTGAGCA
  V  K  S  K  A  G  D  Y  S  T  E  A  R  T  D  N  L  S  E  Q 930                                      960
AGAAAAATTATTACATATGGTATAACTAAACTTCTAAATGGCCAACCAGGGACAACGTGT
  E  K  L  L  H  M  V

990
CAGTTGGGGAGATGAATCTACCAAAACACGTGGTCGTTCC
```

We claim:

1. A purified and isolated DNA molecule consisting essentially of a DNA sequence encoding procine transmissible gastroenteritis virus (TGEV) nucleocapsid protein.

2. A purified and isolated DNA molecule consisting essentially of a DNA sequence encoding procine transmissible gastroenteritis virus (TGEV) matrix (M) protein.

3. A recombinant DNA molecule comprising a DNA sequence coding for the nucleocapsid protein of procine transmissible gastroenteritis virus (TGEV), said sequence being: ATGGCCAACC-AGGGACAACG-TGTCAGTTGG-GGAGATGAAT-CTAC-CAAAAC-ACGTGGTCGT -TCCAATTCCC-GTGGTCGGAA-GAATAATAAC-ATACCTCTTT-CATTCTTCAA -CCCCATAACC-CTCCAACAAG-GTTCAAAATT-TTGGAACT-TA-TGTCCGAGAG -ACTTGTACC-CAAAG-GAATA-GGTAACAGGG-ATCAACAGAT-TGGTTATTGG -AATAGACAAA-CTCGCTATCG-CATGGTGAAG-GGCCAACG-TA-AAGAGCTTCC -TGAAAGGTGG-TTCTTCTACT-ACTTAGGTAC-TGGACCTCAT-GCAGATGCCA -AATTAAAGA-TAAATTA-GAT-GGAGTTGTCT-GGGTTGCCAA-GGATGGTGGCC -ATGAACAAAC-CAAC-CACGCT-TGGTAGTCGT-GGTGCTAATA-ATGAATCCAA -AGCTTGAAA-TTCGATG-GTA-AAGTGCCAGG-CGAATTTCA-CTTGAAGTTA -ATCAATCAAG-AGACAATT-CA-AGGTCACGCT-CTCAATCTAG-ATCTCGGTCT -AGAAATAGAT-CTCAATC-TAG-AGGCAGGCAA-CAATTCAATA-ACAAGAAGGA -TGACAGTGTA-GAACAAGCTG-TTCTTGCCGC-ACTTAAAAAG-TTAGGTGTTG -ACACA-GAAAA-ACAACAGCAA-CGCTCTCGTT-CTAAATCTAA-AGAACGTAGT -AACT-CTAAGA-CAAGAGATAC-TACACCTAAG-AATGAAAACA-AACACACCTC -GAAGA- GAACT-GCAGGTAAAG-GTGATGTGAC-AAGATTTTAT-GGAGCTAGAA -GCAGTT-CAGC-CAATTTTGGT-GACACTGACC-TCGTTGCCAA-TGGGAGCAGT -GCCAAG-CATT-ACCCACAACT-GGCTGAATGT-GTTCCATCTG-TGTCTAGCAT -TCTGTTTGGA-AGCTATTGGA-CTTCAAAG-GA-AGATGGCGAC-CAGATAGAAG -TCACGTTCAC-ACACAAATAC-CACTTG-CCAA-AGGATGATCC-TAAGACTGGA -CAATTCCTTC-AGCAGATTAA-TGCCTATGCT-CGTCCATCAG-AAGTG-GCAAA -AGAACAGAGA-AAAAGAAAAT-CTCGTTCTAA-ATCTGCAGAA-AGGTCAGAGC -AAGATGTGGT-ACCTGATG-CA-TTAATAGAAA-ATTATACAGA-TGTGTTTGAT -GACACACAGG-TTGAGATAAT-TGATGAGGTA-ACGAAC.

4. A recombinant DNA molecule comprising a DNA sequence coding for the matrix protein or procine transmissible gastroenteritis virus (TGEV), said sequence being. ATGAAGATTT-TGTTAATATT-AGCGTGTGTG-ATTGCATGCG-CATGT-GGAGA-ACGCTATTGT -GCTATGAAAT-CCGATACAGA-TTTGTCATGT-CGCAATAG-TA-CAGCGTCTGA -TTGTGAGTCA-TGCTTCAACG-GAGGCGATCT-TATTTG-GCAT-CTTGCAAACT -GGAACTTCAG-CTGGTCTATA-ATATTGATCG-TTTTATAAC-TGTGCTACAA -TATGGAAGAC-CTCAATT-CAG-CTGGTTCGCG-TATGGCATTA-AAATGCTTAT -AATGTGGCTA-TTATGGCCCG-TTGTTTTGGC-TCTTACGATT-TTTAATGCAT -ACTCGGAATA-CCAAGTGTCC-AGATATGTAA-TGTTTCGGCTT-TAGTATTGCA -GGTGCAATTG-TTACATTTGT-ACTCTGGATT-ATGTATTTTG-TAAGATCAT -TCAGTTGTAC-AGAAGGACT-

23
AGTCTTGGTG-GTCTTTCAAC-CCTGAAACTA
-AAGCAATTCT-TTGCGTTAGT-GCATTAG-
GAA-GAAGCTATGT-GCTTCCTCTC
-GAAGGTGTGC-CAACTGGTGT-CACT-
CTAACT-TTGCTTTCAG-GGAATTTGTA
-CGCTGAAGGG-TTCAAAATTG-CAGGTG-
GTAT-GAACATCGAC-AATTTACCAA   -AA-
TACGTAAT-GGTTGCATTA-CCTAGCAGGA-

24
CTATTGTCTA-CACACTTGTT    -GGCAA-
GAAGT-TGAAAGCAAG-TAGTGCGACT-
GGATGGGCTT-ACTATGTAAA       -ATC-
TAAAGCT-GGTGATTACT-CAACAGAGGC-
AAGAACTGAT-AATTTGAGTG        -AG-
CAAGAAAA-ATTATTACAT-ATGGTA.
* * * * *